United States Patent
Chang et al.

(10) Patent No.: US 11,191,873 B2
(45) Date of Patent: Dec. 7, 2021

(54) METHOD FOR PROCESSING A BIOMEDICAL MATERIAL BY A SUPERCRITICAL FLUID

(71) Applicant: NATIONAL SUN YAT-SEN UNIVERSITY, Kaohsiung (TW)

(72) Inventors: Ting-Chang Chang, Kaohsiung (TW); Kuan-Chang Chang, Kaohsiung (TW); Chih-Cheng Shih, Kaohsiung (TW); Chih-Hung Pan, Kaohsiung (TW); Chih-Yang Lin, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 652 days.

(21) Appl. No.: 15/819,660

(22) Filed: Nov. 21, 2017

(65) Prior Publication Data
US 2018/0193525 A1     Jul. 12, 2018

(30) Foreign Application Priority Data
Jan. 12, 2017   (TW) ................................. 106101013

(51) Int. Cl.
*A61L 24/00* (2006.01)
*A61L 27/30* (2006.01)
(Continued)

(52) U.S. Cl.
CPC ............ *A61L 27/306* (2013.01); *A61L 15/18* (2013.01); *A61L 15/42* (2013.01); *A61L 17/14* (2013.01); *A61L 17/145* (2013.01); *A61L 24/001* (2013.01); *A61L 24/02* (2013.01); *A61L 27/50* (2013.01); *A61L 29/14* (2013.01);
(Continued)

(58) Field of Classification Search
None
See application file for complete search history.

(56) References Cited

U.S. PATENT DOCUMENTS 5,344,493 A * 9/1994 Jackson ................. B01J 19/126
134/1
5,550,211 A * 8/1996 DeCrosta ........... B01D 11/0203
528/480
(Continued)

FOREIGN PATENT DOCUMENTS

CN       1405212 A      3/2003
CN       1653112        8/2005
(Continued)

OTHER PUBLICATIONS

English abstract translation of CN 1653112 from the European patent office.

*Primary Examiner* — Cachet I Proctor
(74) *Attorney, Agent, or Firm* — WPAT, PC

(57) ABSTRACT

A method for processing a biomedical material using a supercritical fluid includes introducing the supercritical fluid into a cavity. The supercritical fluid is doped with a hydrogen isotope-labeled compound, an organic metal compound, an element selecting from a halogen element, oxygen, sulfur, selenium, phosphorus or arsenic, or a compound containing the element. The biomedical material in the cavity is modified by the supercritical fluid at a temperature above a critical temperature of the supercritical fluid and a pressure above a critical pressure of the supercritical fluid.

7 Claims, 3 Drawing Sheets

(51) Int. Cl.
*A61L 15/18* (2006.01)
*A61L 24/02* (2006.01)
*A61L 31/08* (2006.01)
*A61L 17/14* (2006.01)
*A61L 31/14* (2006.01)
*A61L 15/42* (2006.01)
*A61L 27/50* (2006.01)
*A61L 29/14* (2006.01)

(52) U.S. Cl.
CPC ............ *A61L 31/088* (2013.01); *A61L 31/14* (2013.01); *A61L 2400/18* (2013.01); *A61L 2420/02* (2013.01)

(56) References Cited

U.S. PATENT DOCUMENTS

| | | |
|---|---|---|
| 5,670,102 A | 9/1997 | Perman et al. |
| 9,738,528 B2 | 8/2017 | Lee et al. |
| 2001/0003007 A1* | 6/2001 | Chinn ............... A61L 27/507 427/2.24 |
| 2003/0021825 A1* | 1/2003 | Pathak ............... A61L 27/16 424/423 |
| 2009/0269480 A1* | 10/2009 | Berglund ............ A61L 31/16 427/2.25 |
| 2011/0236256 A1* | 9/2011 | Matthews ............ A61L 2/18 422/33 |
| 2012/0035089 A1* | 2/2012 | Matthews ............ C11D 3/02 510/161 |
| 2017/0165398 A1* | 6/2017 | Cazalbou ............ A61L 27/32 |

FOREIGN PATENT DOCUMENTS

| | | |
|---|---|---|
| CN | 101125936 | 2/2008 |
| CN | 105473499 A | 4/2016 |

* cited by examiner

METHOD FOR PROCESSING A BIOMEDICAL MATERIAL BY A SUPERCRITICAL FLUID

CROSS REFERENCE TO RELATED APPLICATIONS

The application claims the benefit of Taiwan application serial No. 106101013, filed on Jan. 12, 2017, and the entire contents of which are incorporated herein by reference.

BACKGROUND OF THE INVENTION

1. Field of the Invention

The present invention relates to a method for processing a biomedical material and, more particularly, to a method for processing the biomedical material using the supercritical fluid.

2. Description of the Related Art

A biomedical material is natural or an artificial synthesized material with biocompatibility and can used to replace organs with impaired functions or damaged tissues. According to properties of the biomedical material, medical devices with different functions for the corresponding medical uses can be manufactured.

The most important factor of the biomedical material is the biocompatibility. Therefore, chemically inert material without toxicity, immune response inducibility, allergy inducibility and carcinogenicity is usually used as the biomedical material. In fact, for the requirement of the medical devices, the biomedical material may not be the best choice because of its mechanical properties, such as strength, hardness, toughness and plasticity. However, most material with better mechanical properties probably has poor biocompatibility or produce toxic substances during use, and such material is difficult to apply for medical use. To solve this problem, conventional methods for improving mechanical properties of the biomedical material usually start with modifying shaped material, by post processing such as synthesis, coating, plating and plasma spraying to improve the biocompatibility, the biodegradability, the reliability and the performance of the shaped material, increasing quality of the biomedical material.

However, due to the effect of shape, a shaped finished product can not be easily modified even if both manufacturing and modifying techniques are quite improved. Therefore, the biomedical material may probably not have the predetermined performance, uniformity and reliability. Moreover, the conventional methods for improving mechanical properties of the biomedical material are also limited to the necessary condition such as temperature, pressure, chemical properties and surface topography, and thus the improvement of the mechanical properties is still not ideal.

In light of the inconvenience, the conventional methods should therefore be improved to enhance the practicality thereof.

SUMMARY OF THE INVENTION

It is therefore an objective of the present invention to provide a method for processing a biomedical material using a supercritical fluid. Without changing the original procedure, the biomedical material can be modified and thus can have improved performance, reliability, biocompatibility or biodegradability.

One embodiment of the present invention discloses a method for processing a biomedical material using a supercritical fluid. The method for processing the biomedical material using the supercritical fluid includes introducing the supercritical fluid doped with a hydrogen isotope-labeled compound into a cavity. The biomedical material in the cavity is then modified by the supercritical fluid at a temperature above a critical temperature of the supercritical fluid and a pressure above a critical pressure of the supercritical fluid. The method for processing the biomedical material using the supercritical fluid can be used to uniformly or selectively process the biomedical material with any shape.

The hydrogen isotope-labeled compound can be a protium-labeled compound or a deuterium-labeled compound. The hydrogen isotope-labeled compound can be selected from the group consisting of $LiH$, $NaH$, $KH$, $CaH_2$, $MgH_2$, $BeH_2$, $PH_3$, $B_nH_m$, $C_xH_y$, $HF$, $AsH_3$, $AlH_3$, $H_2S$, $H_2Se$, $HCl$, $HBr$, $HI$, $NH_4Cl$, $CO(NH_2)_2$ and $NH_3$.

Another embodiment of the present invention discloses a method for processing a biomedical material using a supercritical fluid. The method for processing the biomedical material using the supercritical fluid includes introducing the supercritical fluid doped with an organic metal compound into a cavity. The biomedical material in the cavity is modified at a temperature above a critical temperature of the supercritical fluid and a pressure above a critical pressure of the supercritical fluid.

A further embodiment of the present invention discloses a method for processing a biomedical material using a supercritical fluid. The method for processing the biomedical material using the supercritical fluid includes introducing the supercritical fluid doped with either an element selecting from a halogen element, oxygen, sulfur, selenium, phosphorus or arsenic, or a compound containing the element into a cavity. The biomedical material in the cavity is modified at a temperature above a critical temperature of the supercritical fluid and a pressure above a critical pressure of the supercritical fluid.

The halogen element is fluorine, chlorine, bromine or iodine.

The method can further include introducing an electromagnetic wave into the cavity, and the biomedical material is modified by the supercritical fluid together with the electromagnetic wave. The biomedical material can be selected from the group consisting of a metal material, a ceramic material, a high molecular material and a biomaterial. The biomedical material can be a finished biomedical material or a semi-finished biomedical material. The biomedical material can be a surgery device, a knee prosthesis, an artificial biological valve, a stent, an orthopedic fixator, a prosthodontic material, a bone cement, a contact lens, an intraocular lens, an artificial blood vessel, a wound dressing, a suture, an implant used in aesthetic medicine, a cornea, a diagnostic tool, a drug delivery vehicle or a biosensor. The biomedical material can be modified by the supercritical fluid at the temperature of 77-1000 K. The biomedical material can be modified by the supercritical fluid at the pressure of 3-1000 atm.

Accordingly, the method for processing the biomedical material using the supercritical fluid according to the present invention can be used to modify the biomedical material, improving the biocompatibility, the biodegradability, the reliability and the performance of the biomedical material.

Therefore, the application of the biomedical material can be increased, and the efficacy of the medical device made of the biomedical material can also be improved.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
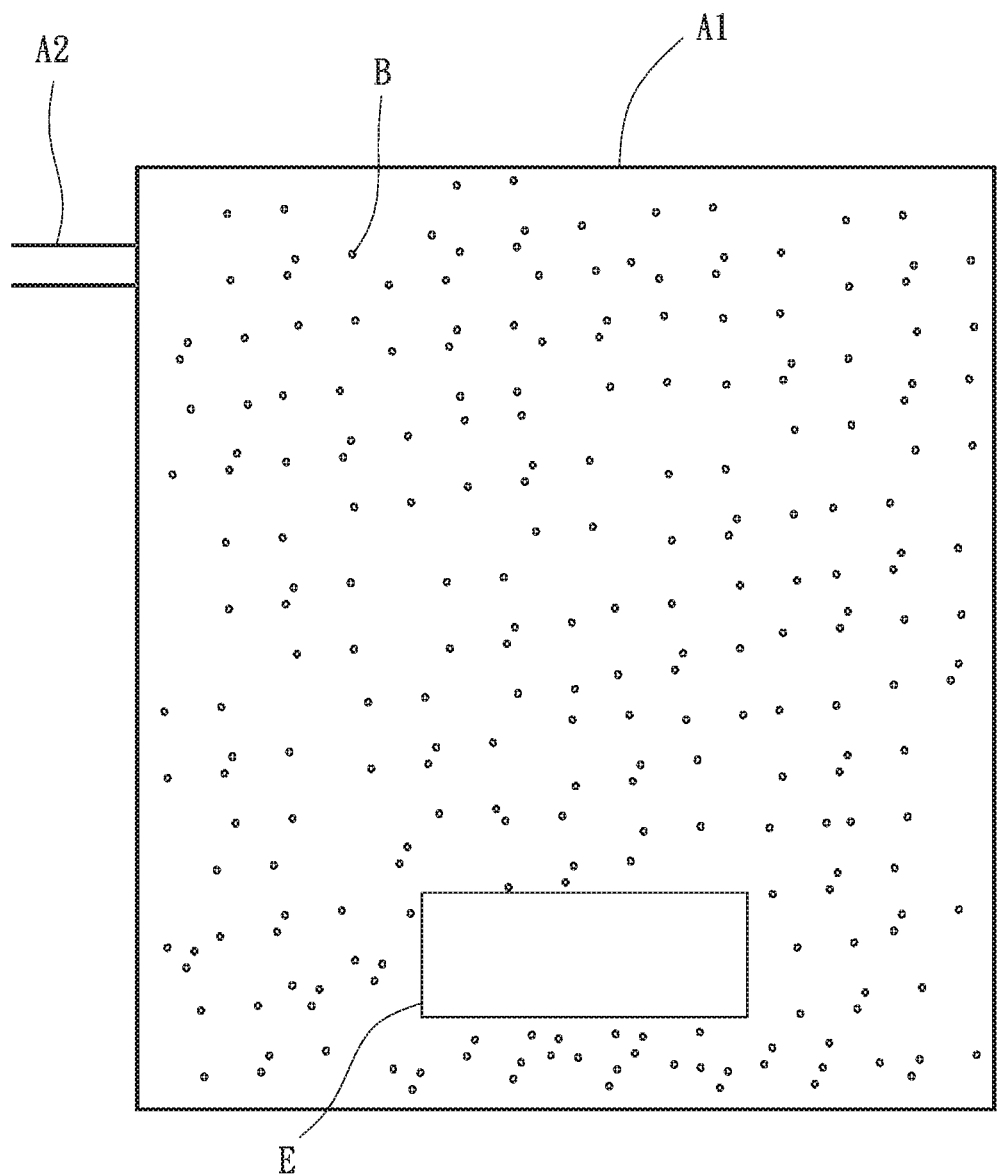
FIG. 1 is a schematic diagram of a method for processing a biomedical material using a supercritical fluid according to the present invention.

FIG. 1 shows a schematic diagram of a method for processing a biomedical material E using a supercritical fluid B according to the present invention. The supercritical fluid B can be introduced into a cavity A1 through a fluid access hole A2. The supercritical fluid B can be selected from, but not limited to, carbon dioxide ($CO_2$), water ($H_2O$), Freon, etc. The critical temperature and critical pressure of carbon dioxide are 31° C. and 72.8 atm, respectively. Therefore, the supercritical carbon dioxide can be formed by pressurization of carbon dioxide at the standard laboratory temperature. Moreover, the critical temperature and critical pressure of water are 374° C. and 218.3 atm, respectively. The supercritical water is a strong oxidizing agent with a high penetrability for modifying at least one biomedical material E.

The biomedical material E can be selected from the group consisting of a metal material, a ceramic material, a high molecular material and a biomaterial. The biomedical material can be a finished biomedical material or a semi-finished biomedical material. As an example, the biomedical material E can be selected from, but not limited to, a surgery device, a knee prosthesis, an artificial biological valve, a stent, an orthopedic fixator, a prosthodontic material, a bone cement, a contact lens, an intraocular lens, an artificial blood vessel, a wound dressing, a suture, an implant used in aesthetic medicine, a cornea, a diagnostic tool, a drug delivery vehicle or a biosensor. The structure of the biomedical material E and the position where defects occur in the biomedical material E can be appreciated by a person having ordinary skill in the art. Therefore, detail description is not given to avoid redundancy.

In this embodiment, as shown in FIG. 1, the supercritical fluid B (such as $SCCO_2$) can be introduced into the cavity A1. The supercritical fluid B can be doped with a hydrogen isotope-labeled compound as a co-solvent. The hydrogen isotope can be a non-radioactive isotope, such as protium or deuterium. As an example, the hydrogen isotope-labeled compound can be selected from the group consisting of LiH, NaH, KH, $CaH_2$, $MgH_2$, $BeH_2$, $PH_3$, $B_nH_m$, $C_xH_y$, HF, $AsH_3$, $NH_3$, $AlH_3$, $H_2S$, $H_2Se$, HCl, HBr, HI, $NH_4Cl$ and $CO(NH_2)_2$. The percentage of the hydrogen isotope-labeled compound can be adjusted according to the requirement. In an alternative example, the supercritical fluid B can be doped with an organic metal compound as the co-solvent. The organic metal compound can be formed, but not to be limited to, from a precursor such as a precursor formed from a chemical reaction. In another alternative example, the supercritical fluid B can be doped with either an element or a compound containing the element as the co-solvent. The element is selected from a halogen element, oxygen (O), sulfur (S), selenium (Se), phosphorus (P) or arsenic (As). The halogen can be fluorine (F), chlorine (Cl), bromine (Br) or iodine (I). In this embodiment, the co-solvent is selected as the hydrogen isotope-labeled compound. Moreover, the at least one biomedical material E in the cavity A1 is modified by the supercritical fluid B at a temperature above a critical temperature of the supercritical fluid and a pressure above a critical pressure of the supercritical fluid B. As an example, the biomedical material E can be modified by the supercritical fluid B at the temperature of 77-1000 K and the pressure of 3-1000 atm.

The characteristics such as density, diffusivity and viscosity of the supercritical phase are between the characteristics of the liquid phase and the gas phase. Therefore, compared to high penetrability and zero solubility of the gas phase and to low penetrability and high solubility of the liquid phase, the supercritical phase (supercritical fluid) possesses both high penetrability and high solubility. Thus, the supercritical fluid B can be used to remove the defects in the material layer of the at least one biomedical material E, to improve the defects in the interface and to modify the thin-layer membrane (such as the change in K value). At the same time, an electromagnetic wave can also be used to improve the modification efficiency. As an example, the electromagnetic wave can also be introduced into the cavity A1, the at least one biomedical material E in the cavity A1 is modified by the supercritical fluid B together with the electromagnetic wave. The specific way to modify the biomedical material E in the cavity A1 can be appreciated by a person having ordinary skill in the art and detail description is not given to avoid redundancy.

Accordingly, after the modification by the supercritical fluid B, the at least one biomedical material E can be used in a state without defects or with a few detects. Therefore, compared to the biomedical material without modification by the supercritical fluid B, the biomedical material E modified by the method according to the present invention has improved biocompatibility, biodegradability, reliability and performance. In a non-restrictive example, the difference between the material properties of the biomedical material E before the modification by the supercritical fluid B and the material properties of the biomedical material E after the modification by the supercritical fluid B is shown in the following description.

Figure 2:
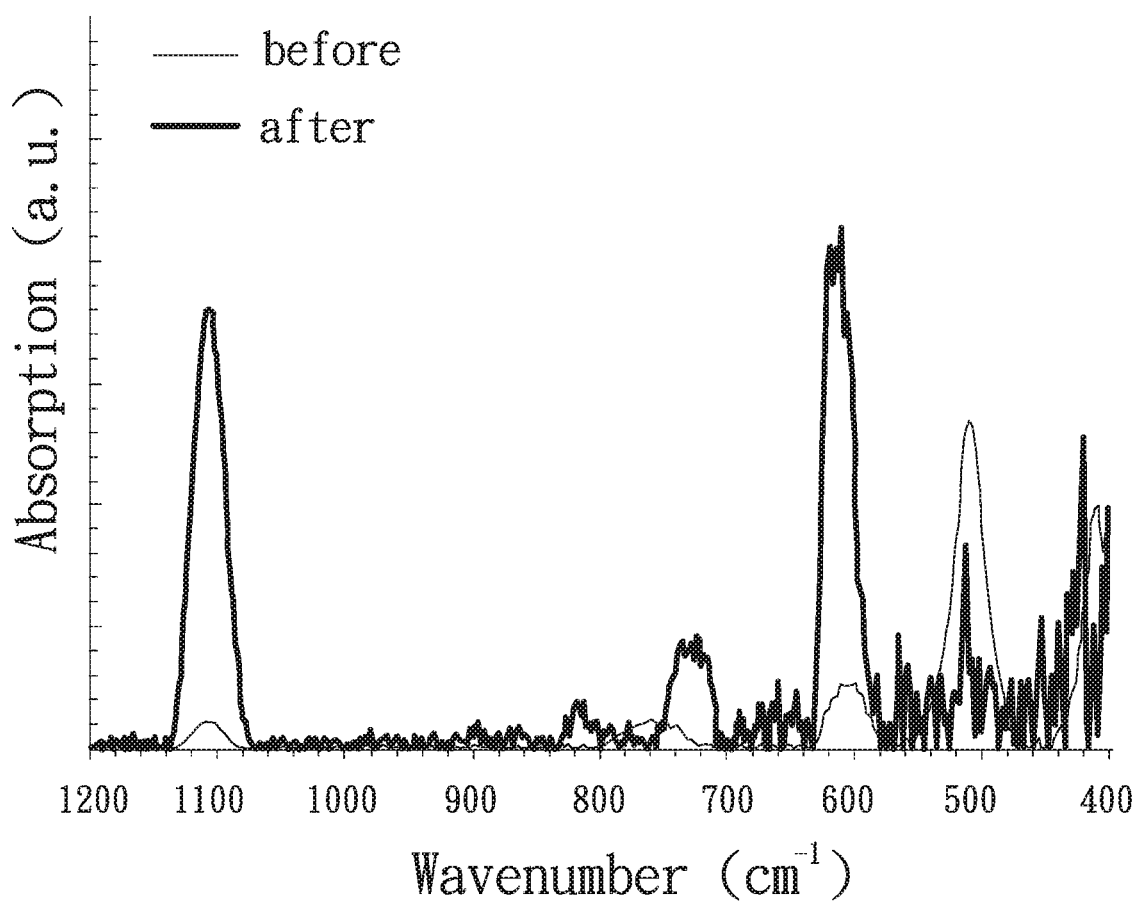
FIG. 2 is a schematic diagram showing by the method for processing the biomedical material using the supercritical fluid according to the present invention, specific functional groups or specific elements on the biomedical material are added or removed after the modification by the supercritical fluid.

Moreover, referring to FIG. 2, the medical material has different properties after the modification by the supercritical fluid. As shown in FIG. 2, specific functional groups or specific elements on the medical material can be added or removed by the supercritical fluid, and the biocompatibility, the biodegradability, the reliability and the performance of the medical material can be therefore improved.

Figure 3:
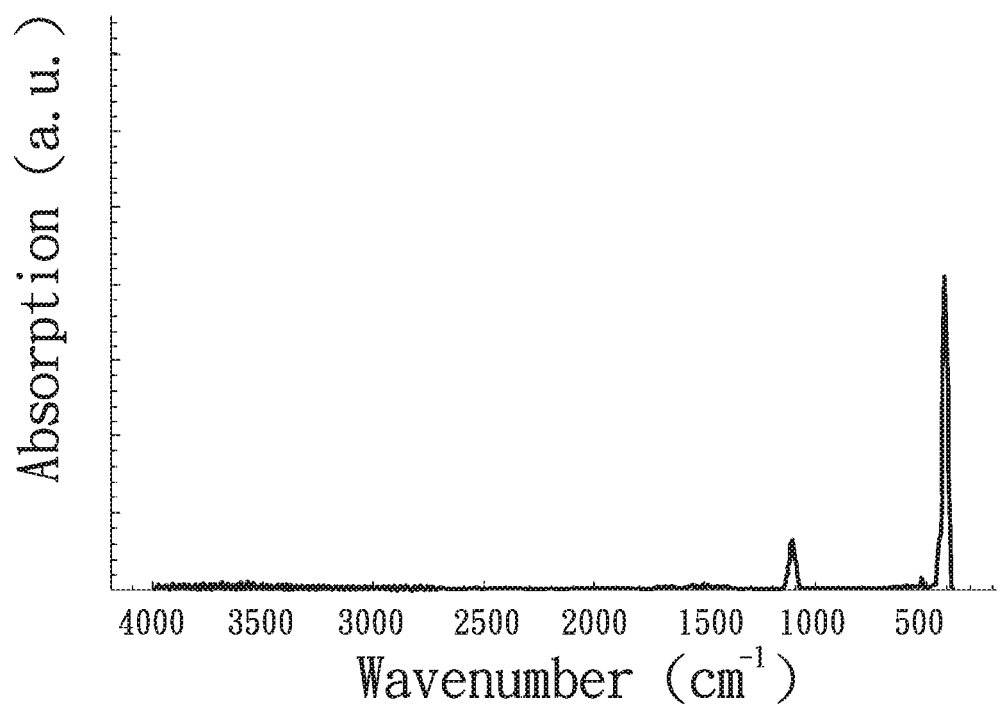
FIG. 3 is a curve diagram showing original properties of the biomedical material before the modification by the supercritical fluid.
Figure 4:
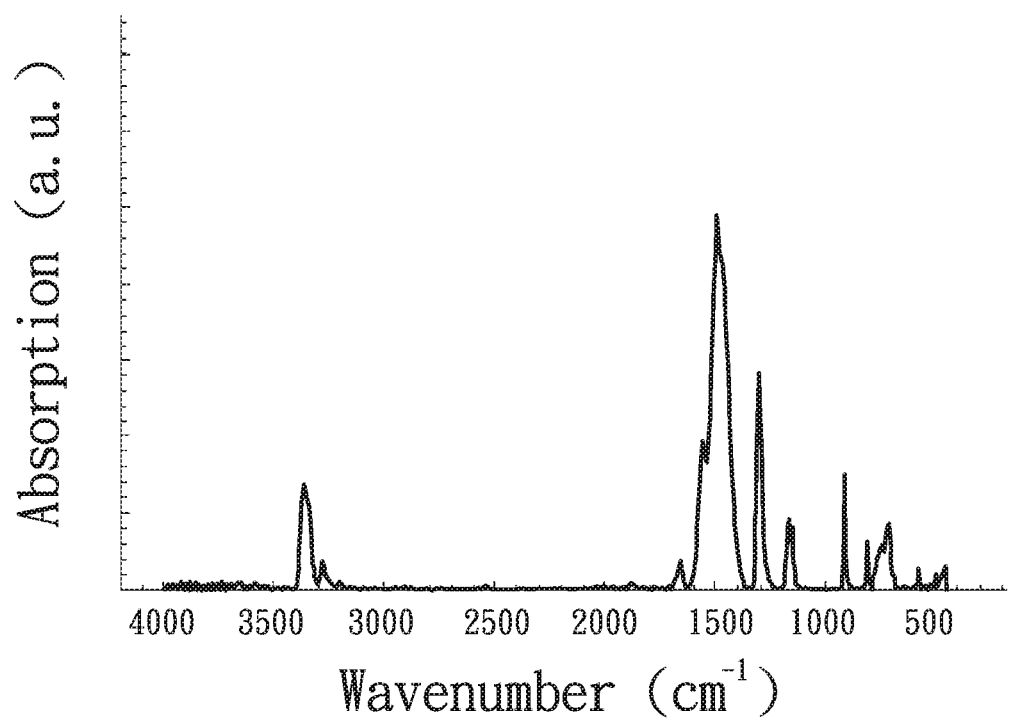
FIG. 4 is a curve diagram showing modified properties of the biomedical material after the modification by the supercritical fluid.

In addition, referring to FIGS. 3 and 4, the modification by the supercritical fluid can indeed effectively modify the biomedical material. Therefore, the application of the biomedical material can be increased, and the efficacy of the medical device made of the biomedical material can also be improved.

Accordingly, the method for processing the biomedical material using the supercritical fluid according to the present invention can be used to modify the defects of the biomedical material E, reducing the interfacial defects and the internal defects. By the method for processing the biomedical material using the supercritical fluid according to the present invention, the specific functional groups and the specific elements on the biomedical material can be added or removed. Therefore, without changing the original procedure, the biomedical material can be modified and thus can have improved biocompatibility, biodegradability, reliability and performance of the biomedical material. Therefore, the application of the biomedical material can be increased, and the efficacy of the medical device made of the biomedical material can also be improved.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for processing a biomedical material using a supercritical fluid, comprising:

adding or removing functional groups or chemical elements on the biomedical material by introducing the supercritical fluid into a cavity having a temperature above a critical temperature of the supercritical fluid and a pressure above a critical pressure of the supercritical fluid;

wherein the supercritical fluid is doped with either a chemical element selected from a halogen element, oxygen, sulfur, selenium, phosphorus, arsenic, or a chemical compound containing the chemical element.

2. The method for processing the biomedical material using the supercritical fluid as claimed in claim 1, wherein the supercritical fluid is introduced into the cavity together with an electromagnetic wave.

3. The method for processing the biomedical material using the supercritical fluid as claimed in claim 1, wherein the biomedical material is selected from the group consisting of a metal material, a ceramic material, a high molecular material and a biomaterial.

4. The method for processing the biomedical material using the supercritical fluid as claimed in claim 1, wherein the biomedical material is a finished biomedical material or a semi-finished biomedical material.

5. The method for processing the biomedical material using the supercritical fluid as claimed in claim 1, wherein the biomedical material is a surgery device, a knee prosthesis, an artificial biological valve, a stent, an orthopedic fixator, a prosthodontic material, a bone cement, a contact lens, an intraocular lens, an artificial blood vessel, a wound dressing, a suture, an implant used in aesthetic medicine, a cornea, a diagnostic tool, a drug delivery vehicle or a biosensor.

6. The method for processing the biomedical material using the supercritical fluid as claimed in claim 1, wherein the cavity has the temperature of 77-1000 K.

7. The method for processing the biomedical material using the supercritical fluid as claimed in claim 1, wherein the cavity has the pressure of 3-1000 atm.

* * * * *